(12) United States Patent
Kino et al.

(10) Patent No.: US 7,067,289 B1
(45) Date of Patent: Jun. 27, 2006

(54) METHOD FOR PRODUCING HISTIDINE BY FERMENTATION WITH E. COLI

(75) Inventors: Kuniki Kino, Chiba (JP); Tetsuya Abe, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/665,617

(22) Filed: Sep. 19, 2000

(30) Foreign Application Priority Data

Sep. 20, 1999 (JP) ............................. 11-265108

(51) Int. Cl.
*C12P 13/24* (2006.01)

(52) U.S. Cl. ................... 435/107; 435/106; 435/252.8

(58) Field of Classification Search ............... 435/106, 435/107, 108, 109, 113, 114, 115
See application file for complete search history.

(56) References Cited

U.S. PATENT DOCUMENTS

| | | | | |
|---|---|---|---|---|
| 4,388,405 A | 6/1983 | Sano et al. | ................. | 435/107 |
| 4,442,208 A | 4/1984 | Tsuchida et al. | ............ | 435/116 |
| 4,463,094 A | 7/1984 | Chibata et al. | ............. | 435/115 |
| 4,504,581 A | 3/1985 | Kurahashi et al. | .......... | 435/107 |
| 4,601,983 A | 7/1986 | Nakamori et al. | .......... | 435/115 |
| 4,775,623 A | 10/1988 | Katsumata et al. | ......... | 435/114 |
| 4,874,698 A | 10/1989 | Ozaki et al. | ................ | 435/108 |
| 4,908,312 A | 3/1990 | Ozaki et al. | ................ | 435/108 |
| 4,927,758 A | 5/1990 | Mizukami et al. | .......... | 435/107 |
| 5,017,483 A | 5/1991 | Furukawa et al. | .......... | 435/115 |
| 5,264,353 A | 11/1993 | Yamada et al. | ............. | 435/115 |
| 5,275,940 A * | 1/1994 | Kino | ......................... | 435/108 |

FOREIGN PATENT DOCUMENTS

| | | |
|---|---|---|
| EP | 0128637 | 12/1984 |
| EP | 0473094 | 4/1992 |
| JP | 50031093 | 3/1975 |
| JP | 77048195 | 5/1978 |
| JP | 81010037 | 2/1981 |
| JP | 60210994 | 10/1985 |
| JP | 61195695 | 8/1986 |
| JP | 61271981 | 12/1986 |
| JP | 2000458 | 1/1990 |
| JP | 2042988 | 2/1990 |
| JP | 4330275 | 11/1992 |
| JP | 93026467 | 3/1993 |

OTHER PUBLICATIONS

Stanbury et al., "Principles of Fermentation Technology", 1984, Pergamon Press, pp. 43-47.*
Patent Abstracts of Japan, vol. 5, No. 164 (C-76)(836) Oct. 21, 1981 & JP-A-56 092 796 (Ajinomoto K. K.) Jul. 27, 1981 *abstract*.
Gerhard Micha, Ed., Biochemical Pathways, John Wiley & Sons, Inc and Spektrum Akademischer Verlag Co-Publication, 1999, p. 1.1.

* cited by examiner

*Primary Examiner*—Irene Marx
(74) *Attorney, Agent, or Firm*—Antonelli, Terry, Stout and Kraus, LLP.

(57) ABSTRACT

The present invention provides a method for producing an amino acid selected from the group consisting of L-alanine, L-valine, L-leucine, L-isoleucine, L-methionine, L-phenylalanine, L-proline, glycine, L-serine, L-threonine, L-cysteine, L-tyrosine, L-asparagine, L-glutamine, L-lysine, L-histidine, L-arginine, L-aspartic acid and L-glutamic acid and useful as medicament, chemical agent, food material and feed additive at high industrial efficiency, the method comprising culturing a microorganism having an ability to produce the amino acid and having resistance to an aminoquinoline derivative in a medium, producing and accumulating the amino acid in the present invention in the culture, and recovering the amino acid from the culture.

1 Claim, No Drawings

METHOD FOR PRODUCING HISTIDINE BY FERMENTATION WITH E. COLI

BACKGROUND OF THE INVENTION

The present invention relates to a method for producing an amino acid by fermentation at high industrial efficiency.

As a direct fermentation method for producing and accumulating L-amino acids directly from saccahride, there have been known methods in which mutant strains derived from wild-type strains of microorganism belonging to the genus *Corynebacterium, Brevibacterium, Escherichia, Serratia* or *Arthrobacter*. For example, the following are known as L-amino acid-producing mutants: auxotrophic mutants which require amino acids, etc. (Japanese Published Examined Patent Application No. 10037/1981), mutants which have resistance to amino acid analogs and vitamins (Japanese Published Unexamined Patent Application Nos. 134993/1981 and 44193/1987), mutants which have both auxotrophic mutation and resistance mutation to amino acid analog (Japanese Published Unexamined Patent Application Nos. 31093/1975 and 134993/1981), mutants which have lowered degradability (Japanese Published Unexamined Patent Application No. 273487/1988, and Japanese Published Examined Patent Application No. 48195/1977), and mutants whose aminoacyl t-RNA-synthesizing enzymes have a decreased substrate affinity (Japanese Published Unexamined Patent Application No. 330275/1992).

It has also been known that the production of an amino acid can be improved by using a transformants obtained by transformation with recombinant DNAs carrying genes involved in the biosynthesis of amino acids (Japanese Published Unexamined Patent Application Nos. 893/1983, 12995/1985, 210994/1985, 30693/1985, 195695/1986, 271981/1986, 458/1990 and 42988/1990; Japanese Published Examined Patent Application Nos. 42676/1989, 11960/1993 and 26467/1993).

For producing L-tryptophan, there has been a report that the productivity of the amino acid was improved by giving resistance to aminoquinoline derivatives or to phenothiazine derivatives (Japanese Published Unexamined Patent Application No. 112795/1992).

SUMMARY OF THE INVENTION

An object of the present invention is to provide an industrially efficient method for producing an amino acid useful as medicament, chemical agent, food material and feed additive.

The present invention relates to the following aspects (1) to (10).

(1) A method for producing an amino acid, which comprises:

(a) culturing in a medium a microorganism having an ability to produce an amino acid selected from the group consisting of L-alanine, L-valine, L-leucine, L-isoleucine, L-methionine, L-phenylalanine, L-proline, glycine, L-serine, L-threonine, L-cysteine, L-tyrosine, L-asparagine, L-glutamine, L-lysine, L-histidine, L-arginine, L-aspartic acid and L-glutamic acid and having resistance to an aminoquinoline derivative in a culture medium;

(b) producing and accumulating the amino acid in the culture; and (c) recovering the amino acid from the culture.

(2) The method for producing an amino acid as described above in (1), wherein the aminoquinoline derivative is selected from the group consisting of chloroquine, amodiaquine, pentaquine, primaquine and the alkali metal salts of these substances.

(3) The method for producing an amino acid as described above in (1), wherein the amino acid is L-histidine.

(4) The method for producing an amino acid as described above in (1), wherein the microorganism is selected from the group consisting of genera *Serratia, Corynebacterium, Arthrobacter, Microbacterium, Bacillus* and *Escherichia*.

(5) The method for producing an amino acid as described above in (4), wherein the microorganism is *Escherichia coli* H-9341 (FERM BP-6674).

(6) A microorganism having an ability to produce an amino acid selected from the group consisting of L-alanine, L-valine, L-leucine, L-isoleucine, L-methionine, L-phenylalanine, L-proline, glycine, L-serine, L-threonine, L-cysteine, L-tyrosine, L-asparagine, L-glutamine, L-lysine, L-histidine, L-arginine, L-aspartic acid and L-glutamic acid and having resistance to an aminoquinoline derivative.

(7) The microorganism described above in (6), wherein the aminoquinoline derivative is selected from the group consisting of chloroquine, amodiaquine, pentaquine, primaquine and the alkali metal salts of these substances.

(8) The microorganism described above in (6), wherein the amino acid is L-histidine.

(9) The microorganism described above in any one of (6) to (8), wherein the microorganism is selected from the group consisting of genera *Serratia, Corynebacterium, Arthrobacter, Microbacterium, Bacillus* and *Escherichia*.

(10) *Escherichia coli* H-9341 (FERM BP-6674).

DETAILED DESCRIPTION OF THE INVENTION

As the microorganism of the present invention, any microorganism can be used, so long as it has an ability to produce an amino acid selected from the group consisting of L-alanine, L-valine, L-leucine, L-isoleucine, L-methionine, L-phenylalanine, L-proline, glycine, L-serine, L-threonine, L-cysteine, L-tyrosine, L-asparagine, L-glutamine, L-lysine, L-histidine, L-arginine, L-aspartic acid and L-glutamic acid (referred to as the amino acid, hereinbelow) and has resistance to an aminoquinoline derivative. Examples of the microorganism includes microorganisms belonging to the genus *Serratia, Corynebacterium, Arthrobacter, Microbacterium, Bacillus* and *Escherichia*, such as *Serratia ficaria, Serratia fonticola, Serratia liquiefaciens, Serratia marcescens, Corynebacterium glutamicum, Corynebacterium mycetoides, Corynebacterium variabilis, Corynebacterium ammoniagenes, Arthrobacter crystallopoietes, Arthrobacter duodecadis, Arthrobacter ramosus, Arthrobacter sulfureus, Arthrobacter aurescens, Arthrobacter citreus, Arthrobacter globiformis, Microbacterium ammoniaphilum, Bacillus subtilis, Bacillus amyloliquefacines* and *Escherichia coli*.

As the aminoquinoline derivative for use in the present invention, any substance can be used, so long as it has the aminoquinoline skeleton. For example, 4-aminoquinoline derivatives such as chloroquine and amodiaquine and 8-aminoquinoline derivatives such as pentaquine and primaquine can be used as the aminoquinoline derivative. Additionally, the alkali metal salts of these substances can be used as the aminoquinoline derivative. All of these substances are known as antimalarial drugs. Herein, any alkali metal such as sodium and potassium can be used as the alkali metals.

The microorganism of the present invention can be obtained by subjecting a microorganism having an ability to produce an amino acid to a conventional mutation treatment including ultraviolet irradiation and treatment with mutagen such as N-methyl-N'-nitro-N-nitrosoguanidine (NTG), culturing the resulting mutant strains under general conditions on an agar plate medium containing an aminoquinoline derivative at a concentration at which the parent strain cannot grow or grow poorly, and selecting colonies of the strain which grow more rapidly than that of the parent strain or colonies which are larger than that of the parent strain among the resulting colonies.

As the microorganism having an ability to produce the amino acid, a microorganism inherently having an ability to produce the amino acid can be used; alternatively, a microorganism which is newly obtained by subjecting a wild-type of a microorganism to produce the amino acid by known methods can also be used.

The known methods include cell fusion method, transduction method, and other gene recombinant techniques [for all, see *Molecular Cloning, A Laboratory Manual, Second Edition*, Cold Spring Harbor Laboratory Press (1989) (abbreviated as *Molecular Cloning, 2nd ed.* hereinbelow)], in addition to the above mutation treatment.

The microorganism of the present invention can also be obtained by preparing a mutant microorganism having resistance to an aminoquinoline derivative by an conventional mutation treatment, followed by subjecting the resulting microorganism to the above-mentioned method to confer on the microorganism the ability to produce the amino acid.

Specific examples of the microorganisms of the present invention include *Escherichia coli* H-9341 (FERM BP-6674).

The production of the amino acid by using the microorganism of the present invention can be carried out by an conventional method for culturing bacteria.

As the medium used for the production of the amino acid, any of synthetic medium or natural medium may be used, so long as it appropriately contains a carbon source, a nitrogen source, an inorganic substance and trace amounts of nutrients which the strain requires.

As the carbon source, carbohydrates such as glucose, fructose, lactose, molasses, cellulose hydrolysates, crude saccharide hydrolysates and starch hydrolysates; organic acids such as pyruvic acid, acetic acid, fumaric acid, malic acid and lactic acid; and alcohols such as glycerin and ethanol can be used.

As the nitrogen source, ammonia; various inorganic salts such as ammonium chloride, ammonium sulfate, ammonium acetate and ammonium phosphate; ammonium salts of organic acids; amines; peptone, meat extract, corn steep liquor, casein hydrolysates, soybean cake hydrolysates, various fermented cells and digested matters thereof can be used.

As the inorganic substance, potassium dihydrogen phosphate, dipotassium hydrogen phosphate, magnesium phosphate, magnesium sulfate, magnesium chloride, sodium chloride, ferrous sulfate, manganese sulfate, copper sulfate, calcium chloride and calcium carbonate can be used.

The microorganism is cultured under aerobic conditions such as shaking culture and aerated agitation culture, at a temperature within a range of 20 to 40° C., preferably within a range of 28 to 37° C. The pH of the medium is within a range of 5 to 9, preferably around neutrality. The pH of the medium is adjusted by using calcium carbonate, inorganic or organic acids, alkali solutions, ammonia and pH buffers.

Generally, the amino acid is produced and accumulated in the medium, by culturing for 1 to 7 days.

After the completion of the culturing, the precipitates such as cells are removed from the medium, and the amino acid can be recovered from the medium by means of ion exchange treatment method, concentration method and salting-out method, etc., in combination.

Any amino acid can be produced, so long as it is the above-mentioned amino acid in the present invention. For example, L-histidine can be produced.

The present invention is further illustrated by the following Examples, which are not to be construed to limit the scope of the present invention.

EXAMPLE 1

Preparation of an L-Histidine-Producing Mutant Strain Having Resistance to an Aminoquinoline Derivative The L-histidine-producing mutant strain H-9340 having resistance to 1,2,4-triazole alanine, which was derived from methionine-requiring *Escherichia coli* ATCC 21318 was subjected to a mutation treatment with N-methyl-N'-nitro-N-nitrosoguanidine (NTG) (0.2 mg/ml, 30° C., 30 minutes) according to a conventional method and spread on a 150 mg/liter primaquine disodium salt-containing agar plate culture medium [0.2% glucose, 0.3% potassium dihydrogen phosphate, 0.6% disodium hydrogen phosphate, 0.01% magnesium sulfate, 0.05% sodium chloride, 0.1% ammonium chloride, 50 mg/liter required nutrient (DL-methionine) and 1.5% agar, pH 7.2].

The bacteria spread on the agar plate medium were cultured at 30° C. for 2 to 6 days, and the growing large colonies were picked up and separated to obtain the strain H-9341. The strains H-9340 and H-9341 were deposited on Mar. 9, 1999 with the National Institute of Bioscience and Human-Technology, Agency of Industrial Science and Technology, MITI (1-3, Higashi 1-chome, Tsukuba-shi, Ibaraki-ken, Japan), under Budapest Treaty with accession Nos. FERM BP-6673 and FERM BP-6674, respectively.

EXAMPLE 2

Comparative Test of Growth on Agar Plate Culture Medium Containing Primaquine

The growth of the mutant strain H-9341 obtained in Example 1 was compared with the growth of the parent strain H-9340 on an agar plate medium containing primaquine.

Each of the mutant strains, which had been cultured in a natural medium for 24 hours and suspended in physiological saline, was spread at a cell density of 1 to 10 cells/cm$^2$ on an agar plate medium containing primaquine disodium salt at the same concentration as that at the time of the acquisition of each mutant strains, and cultured at 33° C. for 4 days.

Growth or non-growth of the strains on the above media is shown in Table 1.

The parent strain H-9340 did not grow on (in) the agar plate culture medium containing primaquine.

TABLE 1

| Bacterial strain | Additives for agar culture medium | |
| --- | --- | --- |
| | No addition | Primaquine disodium salt |
| H-9340 | + | − |
| H-9341 | + | + |

EXAMPLE 3

Production of L-Histidine

The production of L-histidine using the mutant strain H-9341 obtained in Example 1 and the parent strain H-9340 was carried out in the following manner.

Each of the strains H-9340 and H-9341 was inoculated in 6 ml of a seed medium (2% glucose, 0.5% molasses, 1% corn steep liquor, 1.2% ammonium sulfate, 0.3% potassium dihydrogen phosphate, 0.015% magnesium sulfate, 600 mg/liter DL-methionine, 100 mg/liter adenine, 3% calcium carbonate, pH 6.2) in a large test tube, and cultured with shaking at 30° C. for 12 hours.

Each of the obtained seed cultures (0.1 ml) was inoculated in 5 ml of a production medium (6% glucose, 1% corn steep liquor, 2.4% ammonium sulfate, 0.4% potassium dihydrogen phosphate, 0.015% magnesium sulfate, 10 mg/liter thiamine chloride salt, 10 mg/liter calcium pantothenate, 3% calcium carbonate, pH 6.5) in a large test tube and was then cultured therein with shaking at 30° C. for 48 hours.

After culturing, the amount of L-histidine accumulated in the medium was assayed by high-performance liquid chromatography.

The results are shown in Table 2.

Compared with the L-histidine productivity of the parent strain, the L-histidine productivity of the mutant strain H-9341 was improved.

TABLE 2

| Bacterial strains | L-Histidine (g/l) |
| --- | --- |
| H-9340 | 13.0 |
| H-9341 | 14.2 |

In accordance with the present invention, a microorganism having an ability to produce an amino acid selected from the group consisting of L-alanine, L-valine, L-leucine, L-isoleucine, L-methionine, L-phenylalanine, L-proline, glycine, L-serine, L-threonine, L-cysteine, L-tyrosine, L-asparagine, L-glutamine, L-lysine, L-histidine, L-arginine, L-aspartic acid and L-glutamic acid and having resistance to an aminoquinoline derivative can be obtained and by culturing the microorganism in a medium, the productivity of the amino acid can be enhanced so that the amino acid can be industrially efficiently produced.

What is claimed is:

1. A method for producing L-histidine which comprises:
   (a) culturing *Escherichia coli* H-9341 (FERM BP-6674) in a culture medium;
   (b) producing and accumulating L-histidine in the culture medium; and
   (c) recovering L-histidine from the culture medium.

* * * * *